United States Patent [19] [11] Patent Number: 4,524,064
Nambu [45] Date of Patent: Jun. 18, 1985

[54] WOUND-COVERING MATERIALS

[75] Inventor: Masao Nambu, Yokohama, Japan

[73] Assignee: Nippon Oil Company, Limited, Tokyo, Japan

[21] Appl. No.: 497,664

[22] Filed: May 24, 1983

[30] Foreign Application Priority Data

May 26, 1982 [JP] Japan .................. 57-87979

[51] Int. Cl.$^3$ .................. A61K 31/74; A61K 31/78
[52] U.S. Cl. .................. 424/81; 424/78; 514/778; 514/779; 514/781; 514/782; 514/783; 514/944
[58] Field of Search .................. 424/78, 81, 361, 362

[56] References Cited

U.S. PATENT DOCUMENTS 4,010,259 3/1977 Johansson .................. 424/150
4,272,518 6/1981 Moro et al. .................. 424/81

Primary Examiner—Leonard Schenkman
Attorney, Agent, or Firm—Scully, Scott, Murphy & Presser

[57] ABSTRACT

Provided is a wound covering material produced by applying an aqueous solution containing a polyvinyl alcohol with a degree of hydrolysis not less than 95 mol. % and a viscosity-average degree of polymerization not less than 1,500, a water-soluble $C_{2\text{-}20}$ polyhydric alcohol having 2–8 hydroxyl groups in the molecule and a high-viscosity water-soluble macromolecular substance being different from polyvinyl alcohol with a viscosity of the 2% aqueous solution of 25° C. not less than 300 cP, concentrations of said polyvinyl alcohol, said water-soluble polyhydric alcohol and said water-soluble macromolecular substance being adjusted respectively to 1.5–8% by weight, 10–85% by weight and 0.2–15% by weight, onto a flat or curved plate having 30,000–200,000 projections per m$^2$, the total area occupied by the projections being 10–70% to a thickness from 0.5 to 5 mm, cooling the applied plate to a temperature not higher than −6° C. to solidify the solution and then subjecting the resulting mass to vacuum dehydration to a ratio of dehydration from 5% by weight to 95% by weight.

5 Claims, No Drawings

WOUND-COVERING MATERIALS

BACKGROUND OF THE INVENTION

This invention relates to medical materials comprising synthetic macromolecular hydrogels. More particularly, it is concerned with wound-covering materials possessing characteristics far superior to those of prior-art natural or synthetic macromolecular materials.

Hydrogels (hydrous gels) are expected for use as medical materials because of their similarity to living tissues (hydrophilic) in many aspects such as soft touch and low irritation. Known hydrogels, however, find very limited use because, for example, of difficulties in molding due to being too soft or the inferior mechanical strength (see A. S. Hoffman et al., Trans. Amer. Soc. Artif. Intern. Organs, 18, 10 (1972)).

A variety of hardening procedures (means for improving the strength) have been proposed including treatment of mechanically weaker hydrogels with formaldehyde, glutaraldehyde, terephthalaldehyde or the like. However, much cannot be expected from the chemical treatment, the excellent properties of hydrogels (similarity in touch to living tissues, flexibility, elasticity, softness) usually become much worse by such chemical treatment. Moreover, use of a chemical reagent sometimes cause untoward reactions with living tissues (see D. L. MacKenzie et al., A.M.A. Archives Surgery, 77, 967 (1958)).

It is expected that irradiation will be the only means for hardening soft hydrogels without use of the chemical treatment (see N. A. Peppas et al., J. Biomed. Mater. Res., 4, 423 (1977), H. Singh et al., J. Sci. & Ind. Res., 39, March, 162 (1980)). However, the irradiation not only requires special equipment but also its effect is not so remarkable. In general, therefore, its practical application is difficult. By the application of irradiation, moreover, intrinsic superior characteristics of the hydrogels are often lost or deteriorated.

The present invention provides wound-healing cover materials which are superior in mechanical strength, elasticity, softness and touch, produce no irritation on the wound, are non-adhesive and of high permeability for the exudate.

This invention also provides wound-covering materials which, by embedding antimicrobials in the aforesaid hydrogels, have sustained-releasing capacity (long durable release) for the antimicrobial agent embedded to exert antimicrobial activities for a long period of time. In fact, the present invention provides wound-covering materials which effectively and continuously release an antimicrobial agent over a long period of time into the part (area) for which the microbial activities are desired, namely the contact surface of the wound surface with the covering material by embedding the antimicrobial agent in a hydrogel for medical use. There is not employed chemical reaction nor irradiation at all for hardening (improving the mechanical strength) in such a way as in the conventional processes so that no damage is produced on the microbial agent embedded.

Furthermore, this invention provides polyvinyl alcohol-hydrogel cold-preserving materials for medical use suitable for cooling the wound, particularly the wound part immediately after a burn.

The invention also provides wound-healing cover materials which are hardly deteriorated on air-drying after exposure to a lot of exudate (pus), that is, excellent in stability for durable contact with the wound surface.

Polyvinyl alcohol is employed as the starting material for the preparation of the above-mentioned medical materials. Although a number of procedures have been proposed for gelling polyvinyl alcohol (preparation of the hydrogels), all of the procedures involve problems in terms of the operation or of the properties of the product as summarized below.

(1) By air-drying an aqueous solution of polyvinyl alcohol there is obtained a wet or dry film, which, however, is merely a weak film inferior in water resistance and having no rigidity in water which finds only limited applications (see Japanese Patent Publication No. 9523/1965).

(2) Also by adding an acid to an aqueous suspension containing polyvinyl alcohol and tetraethyl silicate and air-drying the resulting mixture there is obtained a similar film to the above under (1) only. In this connection, it has also been proposed to freeze-dry the aqueous suspension to which an acid was added. The resulting film, however, is rather more inferior in strength and is scarcely moldable (see Japanese Patent Publications Nos. 30358/1980 and 11311/1980).

(3) A gelling method involving cobalt-60 ($\gamma$-ray) irradiation of an aqueous solution of polyvinyl alcohol is well known. In this method, however, not only special equipment (equipment for the irradiation) is absolutely needed, so that cost for the irradiation is high, but also an additional hardening means (secondary hardening treatment) should often be applied because the resulting gel is too soft. Therefore, the gel obtained by this method is hardly utilizable except for special applications in which a highly viscous liquid (or a soft gel) is desired such as for the artificial vetreous body (intra-eyeball filling liquid (see J. Material Sci., 1974, 1815)).

(4) Also, it has long been well known that gellation of an aqueous solution of polyvinyl alcohol takes place promptly upon addition thereto of boric acid (or an aqueous solution of boric acid) or borax (or an aqueous solution of borax) (Note: Borax=sodium tetraborate decahydrate). The resulting gel, however, is so weak, fluid and readily splittable merely by touching with fingertips that the molded form is hardly retainable (see J. Am. Chem. Soc., 60, 1045 (1938), French Pat. No. 743942 (1933)).

Moreover, whereas the borax gel can exist under alkaline conditions, it will readily collapse at a pH not higher than 8. Therefore, the gel is hardly utilizable and of little value as medical material.

(5) A number of gellation methods have also been proposed for polyvinyl alcohol by the use of a phenol or an amino compound such as phenol, naphthol or Congo Red or a metallic compound such as of titanium, chromium or zirconium. These methods, however, have the same disadvantages as mentioned above under (4) (see Japanese Patent Publication No.9523/1965).

(6) It is also well known to form gels of polyvinyl alcohol using cross-linking agents or copolymerizing components such as aldehydes, dialdehydes, unsaturated nitriles, diisocyanates, trimethylolmelamine, epichlorohydrin, bis-($\beta$-hydroxyethylsulfone), polyacrylic acid, dimethylolurea and maleic anhydride. In this process, however, not only an operation using chemical reagents is needed, but also it is difficult to obtain a strong gel of a high water content (see Textile Res. J., (3), 189 (1962), British Pat. No.742,900 (1958)).

(7) Also, it has long been well known to form the gels by allowing an aqueous solution of polyvinyl alcohol to stand at a low temperature not higher than 40° C., particularly from 5 to 18° C.

However, the gels formed around room temperature are fragile like agar and carrageenan. Besides, they will be in solution merely by stirring vigorously, by adding water followed by stirring, or by warming gently.

It is also well known that low temperatures are preferable to produce gels from an aqueous solution of polyvinyl alcohol by cooling. For example, it is known to conduct the operation at 18° C., or at a temperature as low as 0° C. or below (see Polymer J., 6, 103 (1974)).

In any case, however, the gels obtained are agar-, carrageenan- or jelly-like weak gels (or viscous liquids) and are very sticky. Moreover, these gels are so poor in water resistance that they will be swollen in water to a remarkable extent, further softened and partly dissolved out into water to leave the remainder in paste. Furthermore, in water or in warm water at 40°-50° C., more rapid deformation takes place to produce an aqueous dispersion or solution. Because of these disadvantages, they have little value as medical materials.

(8) It is also known to prepare gels by adding a small amount of polyvinyl alcohol to an aqueous solution of a water-soluble macromolecular material such as, for example, agarose, agar, albumin, alginate, curdlan, carrageenan, casein, CMC, furcellaran, gelatin, methylcellulose, pectin, starch, tamarind gum, xanthan gum, tragacanth gum and guar gum and allowing the mixture to cool, immersing it in a gellating agent-containing bath (a coagulation bath) or freeze-drying it (see Japanese Patent Publication Nos. 25210 and 25211/1981. By such a process, however, there is obtained merely a weak and poorly water-resistant viscous liquid or non-fluid gel or a loose water-soluble dry powder (freeze-dried powder).

(9) It is also well known that a gel is formed by adding a minimum amount (0.1–0.2% by weight) of polyvinyl alcohol to kaolin or bentonite. On the basis of this principle, a variety of well-known attempts have been made to modify the surface soil of a stadium by scattering polyvinyl alcohol (a diluted aqueous solution) over it to make it less dusty, to improve water permeability or water retention of the field soil by scattering a small amount of polyvinyl alcohol (a diluted aqueous solution) over it, or to promote flocculation and precipitation of clay (colloidal particles) by adding a small amount of polyvinyl alcohol to muddy water. The gels formed by these techniques, however, are also very fragile (hardly distinguishable from soil in appearance) and easily collapse even in dry powder, not to mention in water so that they will poorly be valuable as medical materials.

As a result of studies to develop an inexpensive and consistent process for preparing water-insoluble gels using polyvinyl alcohol which are high in mechanical strength, elasticity and softness, good in touch, excellent in capacity of removing the exudate from the wound part, additionally being non-adhesive to it, will not be stiffened on air-drying, will neither be frozen nor stiffened even when stored in a refrigerator, and will hardly be deteriorated when air-dried after exposure to much exudate from the wound surface (wound part), we have found that the above-mentioned objectives are achieved to give excellent covering materials being non-irritative to the wound part by pouring an aqueous solution containing a polyvinyl alcohol with specific properties, a water-soluble $C_{2-20}$ polyhydric alcohol having 2-8 hydroxyl groups in the molecule and a high-viscosity water-soluble macromolecular substance being different from the polyvinyl alcohol onto a mold having a large number of projections on the surface which solution is cooled, solidified, shaped and then partly dehydrated under vacuum, and completed the present invention.

SUMMARY OF THE INVENTION

This invention provides wound-covering materials which are produced by applying an aqueous solution containing a polyvinyl alcohol with a degree of hydrolysis not less than 95 mol.% and a viscosity-average degree of polymerization not less than 1,500, a water-soluble $C_{2-20}$ polyhydric alcohol having 2-8 hydroxyl groups in the molecule and a high-viscosity water-soluble macromolecular substance being different from the polyvinyl alcohol with a viscosity of the 2% aqueous solution not less than 30 cP (25°C.), concentrations of said polyvinyl alcohol, said water-soluble polyhydric alcohol and said water-soluble macromolecular substance being adjusted respectively to 1.5–8% by weight, 10–85% by weight and 0.2–15% by weight, onto a flat or curved plate having 30,000–200,000 projections per $m^2$, the total area occupied by the projections being adjusted to 10–70% to a thickness from 0.5 to 5 mm, cooling the applied plate to a temperature not higher than $-6°$ C. to solidify the solution and then subjecting the resulting mass to vacuum dehydration to a ratio of dehydration (ratio of weight decrease of the cooled and solidified mass) from 5% by weight to 95% by weight.

DESCRIPTION OF THE PREFERRED EMBODIMENTS

In the present invention, there is no need for use of an acid, alkali, radical source, radiation, organic solvent or reagent which is conventionally used in the prior-art processes for preparing synthetic macromolecular gels. There is also no need at all for hardening treatment to improve the mechanical strength or of any aftertreatment to lower the freezing or stiffening temperature. Moreover, the porous plate (net) gels produced according to the invention are satisfactory in every aspect for the desired capacity of wound-dressing materials. They are provided with rubber-like elasticity and softness, mechanical strength and living tissue-like touch. They produce no irritation in the wouqd part and do not adhere to it. They are of sufficient permeability to remove the exudate. They will not be deteriorated on air drying after exposure to a large amount of the exudate from the wound.

The gels of the invention are also entirely different from the above-described gels produced by cooling an aqueous solution of polyvinyl alcohol in such aspects as being insoluble in cold or warm water and non-sticky. As a matter of fact, the present invention provides novel gels entirely different from the prior-art gels which are formed by allowing an aqueous solution of polyvinyl alcohol to cool or by subjecting an aqueous solution of polyvinyl alcohol to a chemical treatment.

It is required for the polyvinyl alcohol used in this invention to have a degree of hydrolysis not less than 95 mol.%, preferably not less than 97 mol.%. Use of a polyvinyl alcohol with a degree of hydrolysis from 80 to 88 mol.%, particularly not higher than 85 mol % will produce only a weak gel with which the objectives of the invention are not achievable.

The degree of polymerization of the polyvinyl alcohol used in the invention is required to be not less than 1,500. With a degree of polymerization from 300 to 1,500, particularly not higher than 1,400, only a viscous liquid or a weak gel is formed. For example, polyvinyl alcohol with a degree of polymerization from approximately 1,500 to 3,300 may be employed, but the commercially available highly polymerized products (degree of polymerization, 1,500-2,600) are preferably employed as they are.

Initially in the present invention there is prepared an aqueous solution containing a polyvinyl alcohol, a water-soluble polyhydric alcohol and a high-viscosity water-soluble macromolecular substance being different from the polyvinyl alcohol. Concentration of the polyvinyl alcohol may be from 1.5 to 8% by weight, preferably from 2 to 6% by weight. If the concentration is increased to 10% by weight or higher, viscosity of the aqueous solution at ordinary temperature will be increased, or sometimes there will be caused increase in viscosity during storage or degeneration such as solidification in part. As these result in difficulty in handling and a gel being too strong to ensure soft touch, it is preferable for the upper limit not to exceed approximately 8%.

Too low concentration will also cause reduction in mechanical strength of the gel formed. Therefore, it is recommended to fix the concentration to be not less than 1.5% by weight, preferably not less than 2% by weight.

According to the invention, to the aqueous solution of polyvinyl alcohol as described above is added a water-soluble polyhydric alcohol, by which air-drying of the hydrogel after coverage over the wound part for a long period of time is associated with no stiffening. Also due to freeze-point lowering effect of the polyhydric alcohol, storage of the covering material so prepared in a refrigerator is accompanied by no stiffening.

As the polyhydric alcohol containing 2-8 hydroxyl groups in the molecule are usually employed polyhydric alcohols containing approximately 2-20 carbon atoms. Water-soluble polyhydric alcohols having, in addition to the hydroxyl groups, substituents such as carboxyl, acyl, amino, sulfhydryl, imino, carbonyl, alkoxyl, cyano, sulfinyl, mecyl, sulfone, sulfonyl or nitro may be used. Accordingly as the water-soluble polyhydric alcohol of the invention are mentioned, for example, glycerin, 1,2-propyleneglycol, polyglycerin, 1,4-butanediol, 1,3-butanediol, and monosaccharides (erythritol, arabinose, xylose, sylitol, glucose, glucitol (sorbitol, sorbit), gluconic acid, glucuronic acid, glucaric acid, galacturonic acid, fructose, glucosamine. Most preferred are 1,2-propyleneglycol-(propyleneglycol), glycerin and D-sorbitol which are allowed to be used in large amounts as food additives in Japan. These compounds are considered to be acceptable also on the basis of the results of animal experiments on carcinogenicity, acute toxicity, subacute toxicity, chronic toxicity and others (see National Cancer Institute, U.S.A., "Carcinogenicity Data Survey Report", p.417, p.147, p.265 (1975)).

The above-mentioned water-soluble polyhydric alcohol, when prepared in a concentration from 10 to 85% by weight, preferably from 30 to 80% by weight in the aqueous solution and formed in a covering material according to the invention, is embedded in the covering material and not only prevents stiffening of the covering material on air-drying but also contributes to prevention of freezing and stiffening of the covering material of the invention when stored in a refrigerator. Amount of the polyhydric alcohol employed is selected depending upon its capacities such as water retention, moisture absorption and freeze-point depression. For example the, freezing point of the aqueous solution having a propylene glycol content of 35% by weight or 50% by weight is $-15°$ C. or $-34°$ C. respectively, and both are soft at 0° C. Moreover, elasticity, softness and flexibility of the covering material with this glycol embedded remain almost unchanged when air-dried at 37° C. for 20 days. Freezing point of the aqueous solution with a glycerin content of 30% by weight is $-10°$ C. When the covering material of the invention with the glycerin embedded is cooled to 0° C., no stiffening is observed at all. When air-dried at 37° C. for 20 days, it has no tendency of stiffening at all. Also, freezing or hardening point of the aqueous solution containing 32% by weight of glucose, 50% by weight of sucrose, 24% by weight of lactose, 9% by weight of mannitol or 32% by weight of raffinose is $-5°$ C., $-7°$ C., $-2°$ C., $-1°$ C. or $-1°$ C. respectively. The same effects as mentioned above are observed with these formulations.

Previously, we investigated a process for preparing wound-covering materials using a two-component system composed of the polyvinyl alcohol and the water-soluble polyhydric alcohol as described above. The novel water-insoluble gels thereby produced had high mechanical strength, elasticity and softness. They showed good touch and high capacity of removing the exudate from the wound part. Moreover, they were non-adherent to the wound part. They were also hardly stiffened on air-drying, and further neither frozen nor stiffened in a refrigerator. It was also found that excellent results were produced with the covering material in use for deep dermal burn (with much exudate) or traffic wound. Excellent results were confirmed in extensive tests with said covering materials except the situations as specified below. When the covering material was exposed to a large amount of exudate from the wound for a long period of time during which the wound was turned better (the wound was turned dry) while leaving it unchanged throughout the course from long severe wet state to subsequent dry state, there were observed some shrinkage and stiffening (deterioration) of the covering material. There was also tendency for the touch to become worse. These were attributed to elution of the water-soluble polyhydric alcohol from the covering material (gel) due to much exudate (replacement with water content of the exudate) and subsequent evaporation of the water from the covering material in parallel with turn of the wound part to dry state to cause stiffening and shrinkage of the covering material. In such a case, there will be no trouble if the covering material is frequently renewed. Also, the covering material will not be stiffened so far as the wound part remains wet even when exposed to much exudate for a long period of time.

The above-mentioned problems are developed "when the covering material is exposed to a noticeably large amount of the exudate and additionally, the wound part is turned to dry state but left as it is covered while leaving the same covering material unchanged."

As a result of further extensive studies to improve the covering material in this respect, we have found that this objective can be attained by combined use of a high-viscosity water-soluble macromolecular substance different from polyvinyl alcohol with the aforementioned polyvinyl alcohol and water-soluble polyhydric alcohol and completed the present invention. The high-viscosity water-soluble macromolecular substance used in the invention contributes to inhibition of the elution of the polyhydric alcohol caused by a noticeably large amount of the exudate from the wound part. Although mechanism of the contribution of the water-soluble macromolecular substance in the invention is not clear, this may be due to the facts that the polyhydric alcohol dissolved in a viscous aqueous solution of the macromolecular substance in the gel of the invention much reduce the mass transfer (diffusion, elution), that the water-soluble macromolecular substance plugs pores within the hydrogel to inhibit passage (transmission) of the polyhydric alcohol and further that the water-soluble macromolecular substances except for polyvinyl alcohol possess a considerably high water-retaining capacity. On the other hand, the contribution is not remarkable with water-soluble low-molecular compounds.

As the high-viscosity water-soluble macromolecular substance used in the invention is generally usable any of well-known high-viscosity macromolecular substances except polyvinyl alcohol which is unsatisfactory in water retention. For example, natural or synthetic high-viscosity macromolecular substances having a viscosity in 2% aqueous solution not lower than 300 cP at 25° C. such as propylene-glycol ester of alginic acid, tragacanth gum, puleulan, arabia gum, gatty gum, karaya gum, dextrin, starch, Dioscoreaceae mucous substance, mucous Malvaceae, furcellaran, curdlan, methylcellulose, guar gum, locust bean gum, xanthan gum, agar, carrageenan, fucoidin, alginic acid, alginic acid triethanolamine, pectin, agarose, carboxymethylcellulose, tamarind gum, gelatin, polyacrylic acid, sodium polyacrylate, polymethacrylic acid, polyvinylsulfonic acid, polyvinylpyridine, polyethylenimine, vinylimidazole-itaconic acid copolymer, poly(2,4-pentadiene-1-ol) and poly(N-vinyl-2-pyrrolidone) may be mentioned. All of them are effective to achieve the object of the present invention as the molecular weight is high and the aqueous solution is viscous. Viscosity of the aqueous solution is illustrated below. Sodium alginate, 1.5% by weight: 1,100 cP, 2% by weight: 3,730 cP, 3% by weight: 29,400 cP (25.5°C.), carrageenan 2% by weight: 390 cP, 3% by weight: 4,400 cP, 4% by weight: 25,356 cP (25.5°C.), guar gum 0.5% by weight: 1,350 cP, 1% by weight: 3,000 cP, 5% by weight: 510,000 cP (25.5°C.), locust bean gum 2% by weight: 1,100 cP, 3% by weight: 8,200 cP, 5% by weight: 120,000 cP (25.5°C.), propylene glycol ester of alginic acid 1% by weight: 400 cP (25°C.), xanthan gum 1% by weight: 1,100 cP (25°C.), i-carrageenan 1.4% by weight: 4,000 cP (25°C.). As compared with the aqueous solution of a polyhydric alcohol alone, for example, glycerin viscosity of the aqueous solution of which is 4.7 cP at 20° C. for 40% by weight, 6 cP at 20° C. for 50% by weight, 2.3 cP at 30° C. for 60% by weight, 112 cP at 20° C. for 85% by weight or 163 cP at 25° C. for 90% by weight, their solutions are far more viscous.

Whereas a large number of well-known water-soluble macromolecular substances are useful in the present invention, in collective consideration of the touch (feeling), mechanical strength and elasticity of the gel produced according the formulation of the invention and water-retaining capacity and touch particularly when the gel is contacted with a large amount of the exudate for a long period of time and when it is subsequently put in air-drying state, preferable are puleulan, xanthan gum, tragacanth gum, carboxymethylcellulose, polyacrylic acid, i-carrageenan, λ-carrageenan and propylene glycol ester of alginic acid and especially preferable are i-carrageenan, propylene glycol ester of alginic acid, λ-carrageenan and polyacrylic acid. As water-soluble macromolecular substances are generally apt to be contaminated with microorganisms, food preservative additives, that is, antimicrobial agents such as sodium benzoate, calcium sorbate, p-oxybenzoic acid derivatives, sodium dehydroacetate and dehydroacetic acid may be employed.

Amount of the above-mentioned water-soluble macromolecular substance is selected in consideration of the viscosity, solubility, water-absorbing or -retaining capacity and other properties of a particular substance. As described above, concentration in the aqueous solution is adjusted to be between 0.2 and 15% by weight, preferably between 2 and 5% by weight.

In preparing an aqueous solution containing polyvinyl alcohol, a water-soluble polyhydric alcohol and a high-viscosity water-soluble macromolecular substance different from the polyvinyl alcohol, the polyvinyl alcohol, the water-soluble polyhydric alcohol and the water-soluble macromolecular substance may be added to and dissolved in water, and other methods may be employed, for example, the polyvinyl alcohol is dissolved in water in advance, and with the resulting solution are mixed the polyhydric alcohol (or its aqueous solution) and the water-soluble macromolecular substance (or its aqueous solution), or the polyhydric alcohol and the polyvinyl alcohol (or an aqueous solution thereof) are added to and dissolved in an aqueous solution of the water-soluble macromolecular substance. In any of these methods, final adjustment is to give the polyvinyl alcohol in a concentration from 1.5 to 8% by weight, the water-soluble polyhydric alcohol in a concentration from 10 to 85% by weight and the water-soluble macromolecular substance in a concentration from 0.2 to 15% by weight. In carrying out these methods, polyvinyl alcohol which is sparingly soluble in solvents other than water is in dispersion of transparent microgel tiny particles (in transparent aqueous suspension) in the water-soluble polyhydric alcohol- and the water-soluble macromolecular substance-containing aqueous solution. However, this is not an obstacle to carrying out the present invention at all.

Usually in the present invention, the above-mentioned polyvinyl alcohol, polyhydric alcohol and water-soluble macromolecular substance are subjected to sterilization procedure. High pressure-steam sterilization is convenient and effective for the purpose.

Application of the high-pressure steam sterilization (heating) process to the mixed suspension system of polyvinyl alcohol, a water-soluble polyhydric alcohol, a water-soluble macromolecular substance and water, by which the polyvinyl alcohol, the polyhydric alcohol and the water-soluble macromolecular substance will be in aqueous solution, can concurrently be preparation of the starting aqueous solution of the invention and its sterilization.

In the present invention, an aqueous solution comprising polyvinyl alcohol, a polyhydric alcohol and a water-soluble macromolecular substance sterilized by the method as described above is poured onto a plate having projections on the surface to apply the solution on said surface, cooled to solidify it and partially dehydrated under vacuum. As the plate with projections is employed a flat or curved (corrugated) plate provided with 30,000-200,000 projections per m$^2$ in order to form, when molded, a hydrogel net (covering material of the invention) with a mesh for positive use as passage for rapidly eliminating the exudate from the wound part. If the density of the projections is too small, the exudate is apt to be retained in the wound part thereby not only making cure of the wound difficult but also increasing or aggravating contamination to delay the cure. Therefore, the distance between the projections is set to be usually not longer than 2.5 cm, preferably not longer than 0.5 cm, and the number of the projections is set to be not less than 30,000, preferably not less than 50,000 per m$^2$. On the other hand, if the density of the projections is too large, mechanical strength of the molded hydrogel (covering material) is reduced.

As for the size of the projection, too small size is unfavorable, because size of the mesh in the molded hydrogel (covering material) will be too small, and passage and elimination of the exudate from the wound part will be hindered. Therefore, the projection size is usually not less than 1 mm, preferably not less than 1.5 mm. Mbreover, in view of need for rapid elimination and passage of the exudate, total area occupied by the projections should be not less than 10% of the whole surface of the plate. In addition, as the covering material of the invention is applied on the surface of the wound and covered with a water-absorbing material (gauze or bandage), and direct contact of the gauze or bandage with the wound surface should be avoided, size of the projection is not larger than 1 cm, preferably not larger than 7 mm, and it is preferable that number of the projections is not more than 200,000 per m$^2$ and total area occupied by the projections is not more than 70% of the whole surface of the plate.

In the present invention, total area of the projection part is preferably from 20 to 50%.

Height of the projection may be, for example, from 0.01 to 5 mm depending upon the desired thickness of the molded gel.

The material for the projection and the plate with projections may be of any shaped material representatives of which are polyethylene, polypropylene, polystyrene, teflon, steel, aluminum, cast iron and silicone.

In the present invention, an aqueous solution of polyvinyl alcohol, a polyhydric alcohol and a water-soluble macromolecular substance is poured onto a plate provided with projections as described above or applied to the same by means of a spatula. Thickness of the application is from 0.5 to 5 mm, preferably from 1 to 3 mm. This application may be in the same height as that of the projection. When the applied aqueous solution of polyvinyl alcohol and a polyhydric alcohol is cooled, solidified, molded and partially dehydrated according to the invention, shrinkage in the direction of thickness is about 3-8%, by which shrinkage openings corresponding to the projection density are provided. However, care should be paid not to make the application exceeding height of the projection, because desired openings (molding of a porous plate gel) often will not be produced.

According to the invention, the above-described application is followed by cooling and molding of the applied surface. As the cooling agent may be used, for example, a freezing mixture such as sodium chloride - ice (23:77) (−21°C.) or calcium chloride - ice (30:70) (−55°C.), dry ice - methyl alcohol (−72°C.) or liquid nitrogen (−196°C.), thereby cooling to a temperature not higher than −6° C. to attain solidification. If the cooling is insufficient, mechanical strength of the gel produced by the partial dehydration step as described below will be inferior. Use of liquid helium will produce cooling to −269° C. However, this is not only unfavorable from an economical point of view but also produces no advantage on quality of the gel. For practical purpose, it is preferable to use a Freon freezer, for example, to cool to a temperature from −20 to −80° C. The cooling temperature has an influence upon strength of the gel obtained in the below-described partial dehydration step. If a rubber-like elastic gel is desired, preferred temperature is, for example, in the range between −20 and −55° C. Cooling to a temperature from −6 to −20° C. will induce a somewhat decreased strength of the gel. Omitting the cooling and molding, there will be produced a paste-like gel with no stiffness in water at all only but not a rubber-like hydrogel rich in elasticity as in the present invention.

Cooling rate in the molding of the invention may be either a slow cooling at a rate from 0.1° to 7° C./min. or a rapid cooling at a rate from 7° to 1,000° C./min.

According to the invention, the above-described cooling treatment is followed by dehydration under vacuum. Higher ratio of the dehydration (ratio of weight decrease of the cooled and solidified gel) results in higher mechanical strength of the gel. In consideration of the use as a covering material, there is no need for so much increasing the hydration rate to produce a very strong gel. It is preferred to keep softness of the gel by producing a rate of dehydration from 5 to 95% by weight, preferably from 10 to 80% by weight, more preferably from 15 to 70% by weight. The dehydration under vacuum means dehydrate under reduced pressure, which pressure is not limited to a particular degree. For example, the dehydration may be conducted at a reduced pressure not higher than 10 mmHg, preferably not higher than 1 mmHg, more preferably not higher than 0.1 mmHg.

The dehydration step cannot be omitted. As a matter of fact, without dehydration step there will not be produced a gel rich in elasticity and excellent in mechanical strength as in the present invention. As the dehydration proceeds, strength of the gel is very much increased and moreover, such properties as non-stickiness and water resistance are much improved. The partial dehydration step is therefore essential in the present invention. On the other hand, in the invention there is no need for carrying out the dehydration (drying) step to such a degree as in freeze-drying of injectable drugs or in freeze-drying of water-containing food such as coffee, milk, fruit juice or noodles. The objective of the invention is achievable by a partial dehydration treatment as described above. Since strength of the gel is much increased as the dehydration proceeds as described above, degree of the dehydration may be determined depending upon desired strength of the gel.

In any case, the partial dehydration treatment is indispensable and very meaningful in the present invention. Without it, there will no longer obtained non-fluid, non-sticky and high water-content hydrogels with an excellent mechanical strength.

The gel of the invention formed after carrying out the partial dehydration treatment can easily be removed from the above-mentioned plate with projections, and as it is, may directly be used for covering the wound. If required, sterilization treatment with gaseous propylene oxide may be applied for use to cover the wound. Also, it may be placed and sealed in a polyethylene bag which is allowed to stand at room temperature or stored in a refrigerator before use as the wound-covering material.

The gel according to the present invention, despite high contents of the water-soluble polyhydric alcohol, the water-soluble macromolecular substance and water, by far surpasses in mechanical strength polysaccharide gels such as devil's tongue jelly, agar, alginic acid, carrageenan, guar gum and agarose, and protein gels such as soybean cake and jelly. It rather resembles the muscles of human beings and animals. When it is squeezed firmly, it is temporarily deformed but immediately reverted to its original shape. It never gets out of shape.

Even when pressure is applied to the gel of the present invention, liquid contained therein is scarcely exudated. For example, under a compressive stress of 2 kg/cm$^2$, the exudate (eluate) reaches as low as 1–2% of the liquid content.

When the gel of the invention was immersed in tap water for a period of one year, it was not dissolved in and underwent no change in elasticity and mechanical strength. (This is in striking contrast to the results with devil's tongue jelly, which was remarkably mis-shapen when immersed in tap water for several days.)

In the present invention, polyvinyl alcohol is used as an element of the gel (gelling component). However, there may be co-existent other inorganic or organic substances in the present invention, so far as they do not inhibit gel formation of polyvinyl alcohol. Amount of the co-existing substances may be, for example, not larger than a half the weight of polyvinyl alcohol.

Touch of the gel of the invention resembles that of slices of raw squid, fish meat, rice cake, fish paste, cake of pounded fish, "shao-mai" or sausage. The gel of the present invention, which has a touch similar to that of living tissues, is therefore utilizable as a wound-covering material which has such advantages as being rich in elasticity, good in touch, non-irritative and non-adhesive to the wound part.

In the present invention, antimicrobial agents may be added to a mixed aqueous solution of polyvinyl alcohol, a polyhydric alcohol and a water-soluble macromolecular substance. The addition process is conveniently after sterilization of said mixed aqueous solution. As for the case with a heat-resistant antimicrobial agent, it may be added to said mixed aqueous solution followed by steam sterilization under pressure and subsequent application of the gelformation procedures (cooling, solidification and partial dehydration under vacuum) of the invention in the same way as set forth above. There is also obtained a wound-covering material rich in elasticity and good in touch. As the antimicrobial agents usable for this purpose are mentioned, for example, sulfadiazine, silver sulfadiazine, benzalkonium chloride, cetalkonium chloride, methylbenzethonium, neomycin sulfate, hexachlorophene, eosin, penicillin G, cephalothin, cephaloridine, tetracycline, lincomycin, nystatin, kanamycin, penicillinase-resistant penicillins, fradiomycin sulfate and silver lactate used alone or in combination. Among the antimicrobial agents, sodium sulfadiazine is soluble in water in a concentration as high as 50% by weight, whereas sulfadiazine is soluble as low as 1 g per 13,000 ml of water. In the present invention, however, the antimicrobial agent may not necessarily be used in aqueous solution. It may be embedded in the gel (covering material) of the invention by adding with mixing powders or a suspension of an antimicrobial agent to a mixed aqueous solution of polyvinyl alcohol, a polyhydric alcohol and a water soluble macromolecular substance.

Amount of the antimicrobial agent added to the mixed aqueous solution of polyvinyl alcohol, a polyhydric alcohol and a water-soluble macromolecular substance according to the invention may be not higher than a half the weight of the polyhydric alcohol. For example, 0.2–4% by weight of fradiomycin sulfate, 1–25% by weight of sulfadiazine or 0.2–1% by weight of penicillin G may be employed. The antimicrobial agent embedded in the gel of the invention is not eluted in a short period of time but is maintained embedded and slowly released over a long period of time. For example, when 5 g of the gel obtained by the process of the present invention after dissolving sodium sulfadiazine in a mixed aqueous solution of polyvinyl alcohol and a polyhydric alcohol in a concentration of 3% by weight is immersed in 5 ml of physiological saline solution for 6 hours, about 15% of the sodium sulfadiazine is eluted (lost). When the resulting gel is immersed in another 5 ml of physiological saline solution for 3 days, the sulfadiazine is continuously released with 35% of the originally embedded amount left unreleased in the gel. In the present invention, therefore, amount of the antimicrobial agent embedded is conveniently determined in consideration of the slow release rate of a particular antimicrobial agent as well as of severity of the infected wound, progress of the therapy, adverse reactions of the antimicrobial agent, and also of the concurrent therapy (that is, for example, chemotherapy by application of an antibiotic-containing ointment to the wound surface or the covering material of the invention).

In the present invention, there is no need to take care of contamination of the hydrogel of the invention with hazardous substances so long as steam sterilization under pressure of the mixed aqueous solution of polyvinyl alcohol, a polyhydric alcohol and a water-soluble macromolecular substance is carefully conducted, and the cooling, solidification and partial dehydration under vacuum are made aseptically, because there is used none of hazardous reagents or solvents in the course of preparation of the hydrogels. Also in the case where an antimicrobial agent is embedded in the gel of the invention, there is no possibility for hazardous substances to be accompanied by so long as the nature and embedded amount of the antimicrobial agent are suitably selected, and rather there is produced a cure-promoting effect for the infected wound by the embedded antimicrobial agent.

The mechanism of producing a hydrogel of high mechanical strength and elasticity and good touch entirely different from known polyvinyl alcohol gels by cooling, molding and partially dehydrating an aqueous solution of polyvinyl alcohol, a polyhydric alcohol and a water-soluble macromolecular substance according to the present invention is not clear. This may be ascribed to formation of a large number of intramolecular and intermolecular hydrogen bonds in the polyvinyl alcohol in the course of cooling, molding and subsequent partial dehydration treatments and increased crystallinity of the gel structure especially during the partial dehydration which in turn increase the mechanical strength and elasticity.

In any way, the cooled and partially dehydrated gels of polyvinyl alcohol and the process for preparing the same are novel ones first found by us.

Mechanical strength of the polyvinyl alcohol according to the invention is further increased by applying a hardening treatment known to polyvinyl alcohol fibers or films. As the known hardening (bridging) treatments are mentioned those using aldehydes, dialdehydes, diisocyanates, phenols, or metallic compounds such as of titanium, chromium and zirconium, and furthermore borax, acrylonitrile, trimethylolmelamine, epichlorohydrin, bis($\beta$-hydroxyethyl)sulfone, polyacrylic acid, dimethylolurea or maleic anhydride. These secondary hardening treatments are not particularly required for the gels of the invention because of the high mechanical strength as described above.

As described above, the porous plate (net) hydrogels of the present invention which are non-irritant when contacted with living tissues, non-adhesive to the wound part, and of good touch and satisfactory mechanical strength and elasticity, and also good in permeation (passage) of the exudate from the wound part, are useful as the covering material for a variety of injuries such as wounds and burns. They are especially valuable for the therapy of contaminated injuries.

The wounds as referred to in the present invention are open wounds among the injuries of living tissues caused by external injuries or surgical operations. That is to say, wounds in more or less diastatic state caused by the dysjunction of a part of the skin or body surface covered with the mucosa owing to an external force exceeding the resistance of the living tissue are referred to. An incision by a scalpel or a knife, a stab by an injection needle, a sewing needle or a pocketknife, a break by a thick-edged tool such as an axe, a sprain by a dull force to cause crushing of the living tissue, a laceration by abnormal stretching or elongation of the living tissue, a bite, a bullet-wound, an injury of the skin with a chemical such as sulfuric acid, hydrochloric acid or sodium hydroxide, a burn, a chilblain, an electric injury by high-voltage electric current or an acute injury by radiation may be mentioned.

Suppurated wounds as referred to in the invention include not only wounds excreting a large amount of exudate or pus but also wounds with high possibility of being infected, typical of which are second-degree deep dermal burn, third-degree burn and third-degree deep dermal burn. For example, the second-degree deep dermal burn for which therapy for a period not shorter than three weeks is usually needed without infection at the initial stage is often converted (aggravated) to more severe third-degree burn due to suppuration despite intended inhibition of the infection. As stated above, when microbial proliferation is considered to be highly possible though not initially suppurated, initial treatment in the same way as in the infected wound is needed. That is, sufficient removal of the exudate and, as needed, application of an antimicrobial agent is necessary for early cure. Definition of the suppurated wound (infected wound) set forth above in the present invention is a proper one from the practical therapeutic point of view.

In the therapy of infected wounds (contaminated wounds) it is indispensable to avoid retention of the exudate in the wound part (to remove or absorb the exudate, and depending upon the symptoms, debride the slough). In such a case, even if the exposure method in which the burn is exposed to air after application of an antimicrobial agent is applied to the wound part, bacteria are proliferated in the exudate from the wound part thereby accelerating suppuration. Also by a method involving application of gauze to the wound part and coverage with an oiled paper and a method by covering the wound part with a synthetic or natural macromolecular film (occlusive method) the condition is apt to be aggravated unless the exudate from the wound part is thoroughly removed. As seen from the above description, the aforementioned treatment by rapid absorption and removal of the exudate is strongly desired for the infected wound, for which treatment a covering material of a high liquid-removing capacity is required.

The wound-covering material according to the present invention is useful not only for covering wounds which are almost impossible to be infected during the treatment (slight and fresh) but also for covering suppurated wounds referred to above which need a long duration of treatment during which the exudate from the wound part should continuously be removed. In either case, the covering material of the invention is applied to the wound part, followed by coverage of the applied part with gauze (and bandage), thereby passing the exudate from the wound part through the network of the covering material to the gauze and absorbing it. In such treatment, chemotherapy by applying an antibiotic-containing ointment may be combined, but application of a large amount of the ointment should not be done for facilitating passage and removal of the exudate.

Application of the covering material to the wound part always produces good touch, non-irritation and removal of the exudate through the network of the covering material. There is accompanied no adherence of the covering material to the wound part. Most important for the therapy of wounds, either suppurated or non-suppurated, is prevention of infection, for which the exudate should not be retained in the wound part but should be removed and absorbed. Non-irritation to the wound part and good touch are also desired. Besides, the covering material should not be adhered to the wound part. As described later, most of the prior-art gauze, natural macromolecular materials and synthetic macromolecular materials had a tendency of adhering to the wound part. Consequently, they had such disadvantages as giving pain to the patient and causing hemorrhage and re-injury in the wound part when peeled off.

Unlike these prior-art products, the present invention provides covering material for the treatment of wounds which meet all the requirements at once in terms of mechanical strength, capacity of passing the exudate, elasticity, softness, touch, non-irritation and non-adherence, and also produce the effect of continuously releasing the embedded antimicrobial agent if needed. Besides, as the covering material of the invention is not stiffened (frozen) with the original elasticity and softness kept unchanged when stored in a refrigerator (freezing box), it is effective in keeping the wound part cool as required.

As well known, various wound-covering materials have been proposed. Among them, lyophilized porcine skin, a typical one, is almost always accompanied by infection when applied to deeply injured and retardedly curable wounds. As repeatedly pointed out, it is also not only ineffective but also hazardous for the suppurated wounds.

When used as an adhering and closely sealing material for non-infected wounds, the porcine skin should be renewed every three days because of its readiness to be melted, although it is effective in inhibiting attack of bacteria and relieving pain. It is also disadvantageous in that hemorrhage is caused by close adhesion to the wound part.

Formalized polyvinyl-alcohol sponges cannot be used for the wound surface in which regeneration of the epidermis is expected as the material itself is taken into the wound (part), although they are advantageously capable of preventing infection. It is also pointed out that they are disadvantageous in that they are dried and hardened during use (J. B. Blumberg et al., Ann. Surg., 151, 409 (1960)).

Fibrin membrane is also inferior in liquid-removing capacity and is apt to induce retention of the exudate, infection and melting of the membrane (covering material).

Collagen membrane is readily molten when contacted with the wound part and must be used with care for wounds with much exudate. Polyurethane, polyamino-acid, polyethylene, polyvinyl-chloride or silicone film is also inferior in transmission (passage) of the exudate, softness or durability. Poly(2-hydroxyethyl methacrylate) is inferior in mechanical strength and has a disadvantage that it should be immersed in cold or hot water when peeled off from the wound part.

As described above, whereas all of them are useful for covering (closely sealing or closely adhering to) mild burn (which is not suppurated and expected to be shortly cured without being accompanied by infection), they are no way the material useful in the treatment of every wound. When there is much exudate from the wound part, either infected or non-infected, gauze and bandage are applied, which are often dried and adhered to the wound part, and when exchanged (renewed), are accompanied by hemorrhage or re-injury thereby giving pain to the patient. They are also unsatisfactory in touch and elasticity as the covering material and give feeling of foreign matter.

Natural polysaccharides such as karaya gum have been proposed in order to overcome the above-mentioned difficulties. However, they are readily molten in the wound part to become muddy. Agar is a hydrophilic gel with good touch, but it is fragile and readily got out of shape so that it is not suitable for practical use. Woven stuff of Nylon, polyester, polypropylene, viscose rayon or the like has the same disadvantages as those of gauze. The network of woven stuff is so fine that it is often plugged with pus. It is often adhered to the wound part, and when peeled off, is reported to injure the living tissue again.

Network covering materials using cotton or synthetic polymer threads have also been provided. They are, however, of poorly elastic threads and even if the disadvantage in touch were allowable, they are taken into the wound part, dried and adhered, thereby unavoidably injuring the wound part.

As seen from many examples given above, none of the known wound-covering materials meets all of the requirements in terms, for example, of passage of the exudate (liquid-removing capacity) in the wound part, stability of the material per se (duration of the effect), wet strength, touch, softness, elasticity, non-adherence to the wound part, and sustained release of the drug desired as needed. None of the products is found to be hardly dried, stiffened and adhered during use. On the contrary, the covering materials according to the present invention are highly elastic gels with good touch in which drying and stiffening are prevented by incorporating a large amount of a polyhydric alcohol and a high-viscosity water-soluble macromolecular substance different from polyvinyl alcohol. As they are porous plates (networks), passage of the exudate is not hindered. They possess a wet strength sufficient to be used as a covering material and not only have the capacity of embedding and slowly releasing (sustained release) drugs such as antibiotics but also have many advantages such as non-irritation and non-adhesion to the wound part. By combining with gauze or bandage, they are useful as the covering material for the treatment not only of non-infected wounds but also of remarkably contaminated wounds.

Comparison of the effect of the combination of a high-viscosity water-soluble macromolecular substance different from any of the polyvinyl alcohol and the polyhydric alcohol according to the invention with that of non-use of said water-soluble macromolecular substance is critical for understanding the invention. Details will be given later in Examples and Comparative Examples. An example of the laboratory comparative test will be given below in order to facilitate understanding of the essential feature.

Anount of the exudate from the wound part is reported to be, for example, 0.04–0.4 $g \cdot cm^{-2} d^{-1}$ or 0.06–0.8 $g \cdot cm^{-2} d^{-1}$ (H. N. Harrison et al., Surg., 56, 203 (1964), L. O. Lamke et al., Scand. J. Plast. Reconstr. Surgery, 5, 17 (1971)). In the wound part exuding especially large amount, it is considered to be ca. 1.2 $g \cdot cm^{-2} d^{-1}$. Accordingly in the comparative test described below, rate of supplying a model exudate (sodium chloride 0.9% by weight, albumin 2% by weight, globulin 2% by weight, glucose 0.1% by weight, lactic acid 0.2% by weight, creatinine 10 ppm, urea 0.05% by weight, $NaHCO_3$ 25 mM and $Na_2CO_3$ 25 mM, pH 9.2) is adjusted to 1.2 $g \cdot cm^{-2} d^{-1}$ as cited above.

A net hydrogel composed of 8% by weight of polyvinyl alcohol, 42% by weight of glycerin and 50% by weight of water (covering material containing no high-viscosity water-soluble macromolecular compound) was piled on gauze, followed by piling of filter paper. The above-mentioned model exudate (37° C.) was then sprayed thereover at a flow rate of 1.2 $g \cdot cm^{-2} d^{-1}$. After 24 hours, most of the glycerin in the hydrogel transferred to the gauze to a reduced glycerin concentration in the gel of 4% by weight. When the initial glycerin concentration in the gel was doubled to 84% by weight, elution of the glycerin was also unavoidable, and concentration of the glycerin remaining in the gel after 36 hours was decreased to 4% by weight. The hydrogels from which the glycerin had been eluted were transferred respectively to a dish and allowed to stand in a thermostat for 10 hours, there were observed in the hydrogels symptoms of deformation (shrinkage) and stiffening and some reduction in elasticity.

On the contrary, when a test was conducted by spraying the same model exudate over a hydrogel in which i-carrageenan was incorporated according to the present invention (polyvinyl alcohol 4% by weight, i-carrageenan 8% by weight, glycerin 83% by weight and water 5% by weight), amount of the eluted glycerin was far smaller, the glycerin remaining in the gel in a concentration of 72% by weight. The hydrogel with much glycerin remaining was allowed to stand in a thermostat at 33° C. for 4 days. There was observed little deformation of the gel with no symptom of stiffening. Decrease in weight after the air drying for 4 days was as small as 9% by weight thereby confirming little deformation (evaporation of the water) by air drying.

The net covering material of the invention (polyvinyl alcohol 4% by weight, i-carrageenan 8% by weight, glycerin 83% by weight, water 5% by weight) was contacted with the model exudate for 12 hours in the same way as above. Then, the resulting material was transferred to a dish and allowed to stand at 33° C. for 8 days. There was observed almost no deformation and stiffening of the hydrogel.

As seen from the above results, absence of the water-soluble macromolecular substance of the invention induces elution of the polyhydric alcohol when attacked by a large amount of the exudate for a long period of time, even if amount of the water-soluble polyhydric alcohol embedded is much increased. On the other hand, combined use of the high-viscosity water-soluble macromolecular substance evidently produces such superiorities that elution of the polyhydric alcohol in the gel is much reduced and resistance to air drying is maintained for a long period of time.

Accordingly, when the covering material according to the invention is used, there is no need of frequently renewing the covering material in the severely wound part producing much exudate, and the covering material, gauze and bandage may be exchanged as judged by the physician depending upon production of the exudate while keeping the wound part as clean as possible and allowed as they are for a long period of time after recovery to non-wet condition of the wound part (gauze and bandage).

Examples of the invention will be given below.

EXAMPLE 1

An aqueous suspension composed of 3.4 g of a polyvinyl alcohol having a degree of hydrolysis of 99.5 mol.%, a viscosity-average degree of polymerization of 2,600 and a viscosity of the 4% aqueous solution at 20° C. of 67 cP (water content 7% by weight), 50 g of propylene glycol, 0.8 g of propylene glycol ester of alginic acid and 46 g of water was subjected to steam sterilization under pressure at 120° C. for 30 min. It was then stirred in a sterile room to give an aqueous solution of 3.2% by weight of the polyvinyl alcohol, 50% by weight of propylene glycol and 0.8% by weight of propylene glycol ester of alginic acid. Onto a polyethylene plate with projections (height of the projection 2 mm, density of the projections 120,000/m$^2$, shape of the projection cylinder 2.3 mm in diameter, total area occupied by the projections 50%, size of the plate 12×12 cm) which had been gas sterilized was poured 13 g of the solution, which was evenly applied by means of a spatula (applied thickness 1.8 mm). After being at −50° C. for 0.7 hours (cooling and solidifying molding) and dehydrated under vacuum for 4 hours, there was obtained 8 g of a gel (net) (ratio of dehydration, that is, ratio of decrease in weight of the cooled and solidified product=40% by weight). Apparent tensile strength of the net was as high as 0.7 Kg/cm$^2$. It had elasticity and softness similar to and mechanical strength superior to devil's tongue jelly, compression-resistant strength being 10 Kg/cm$^2$ or higher.

The net (porous plate gel) had a diameter of the opening of 2.3 mm, a pore ratio (area ratio) of 50% and a thickness of ca. 1.7 mm. It was placed in a polyethylene bag (15×20 cm) which had been sterilized with gaseous propylene oxide, and the bag was closely sealed and allowed to stand overnight in a refrigerator (−13° C.).

There was observed no stiffening (freezing) and initial softness and devil's tongue jelly-like softness and touch were kept unchanged. A portion of the net from the polyethylene bag was taken to give a piece 1 cm×1 cm in size, which was placed in a glass dish and allowed to stand open in a thermostat at 37° C. for 4 days. There was maintained the initial weight (55 mg), evaporation loss of the water being as low as 4% by weight (3 mg) or less, and the initial softness and elasticity unchanged.

The above-described cooling, solidification and partial dehydration under vacuum procedures were repeated with the same mixed aqueous solution of the polyvinyl alcohol, propylene glycol and propylene glycol ester of alginic acid to prepare 70 pieces of the same net (covering material) as above.

Six rabbits weighing 1,630–1,870 g were sheared on the back by an electric hair-clipper, which was completely depilated with a depilatory cream. The depilated region was contacted with an electric iron (115° C.) for 10 seconds under nembutal anesthesia to develop burn (second degree, 9×9 cm). The burn was then allowed untreated for 18 hours to induce infection (suppuration). There was observed continued production of much exudate (pus).

To the wound surfaces of two of the rabbits was applied the net covering material of the invention (11×11 cm) respectively, which was covered with gauze and bound by a bandage. The covering material, gauze and bandage were renewed every 24 hours in order to keep the wet wound part as clean as possible. It was confirmed that the pus was smoothly passed through the net and absorbed in the gauze and bandage. There was observed no hemorrhage due to adhesion between the wound part and the gauze or the one between the wound part and the covering material. There was observed no moistness in the bandage and gauze after 7 days, and the wound was judged to have progressed toward recovery (dry state). It was then allowed to stand for additional 13 days without renewal of the covering agent, gauze and bandage. There was observed regeneration of the epidermis around the wound surface on the 23rd day after development of the burn. Thereafter, the ulcerous region became smaller day by day and recovered on the 27th day in the two animals.

COMPARATIVE EXAMPLE 1

The propylene glycol ester of alginic acid used in Example 1 was replaced by a corresponding portion of water, and the same procedures were done to give 8 g. of a gel (net).

The same procedures were repeated to prepare 70 pieces of the same net (covering material).

The net gel (11×11 cm) was applied respectively to the suppurated wound surfaces of two of the rabbits with burn producing much exudate obtained in Example 1. The net was covered with gauze and bound up with a bandage, and the three were renewed every 24 hours. The pus was smoothly passed through the net and absorbed in the gauze and bandage. There was observed no hemorrhage due to adhesion between the wound part and the gauze or the one between the wound part and the covering material in the exchange of the bandage. After 7 days, as there was observed no moistness in the bandage and gauze, the wound was judged to have progressed toward recovery (dry state). It was then allowed to stand for additional 3 days without renewal of the covering material, gauze and bandage. Then, a renewal was attempted to find that deformation of the covering material (unevenly shrinked to ca. 8×8 cm) and a stiffening tendency were observed. It was further found that part of the covering material and the wound part were adhered each other.

As a matter of fact, whereas the gel of the invention in Example 1 was neither deformed nor deteriorated when allowed to stand dry for 13 days after exposure to much exudate, absence of propylene glycol ester of alginic acid, a high-viscosity water-soluble macromolecular substance, evidently causes problems when allowed to stand dry. The latter example indicates that the material is not tolerable to air drying for 3 days.

EXAMPLE 2

An aqueous suspension composed of 5.3 g of a polyvinyl alcohol having a degree of hydrolysis of 97.5 mol.%, a viscosity average degree of polymerization of 2,200 and a viscosity of the 4% aqueous solution (20° C.) of 56 cP (water content 7% by weight), 100 g of glycerin, 10.9 g. of i-carrageenan and 84 g of water was subjected to a pressure steam sterilization at 120° C. for 35 min and then stirred in a sterile room to give an aqueous solution of 2.5% by weight of the polyvinyl alcohol, 50% by weight of glycerin and 5% by weight of i-carrageenan.

Onto a stainless steel plate with projections (height of the projection 1.5 mm, density of the projections 74,000/m², shape of the projection cylinder 1.8 mm in diameter, total area occupied by the projections 20% and size of the plate 48 cm×27 cm) which had been steam sterilized was poured 135 g of the aqueous solution, which was evenly brushed (applied) by an aluminum plate (27 cm×4 cm×0.1 cm) to a thickness of 1.3 mm. Cooling at −60° C. for 0.7 hour (solidification and molding) and dehydration under vacuum for 5 hours gave 95 g of a gel (ratio of dehydration 30% by weight). Apparent tensile strength of the net was as high as 1.1 Kg/cm². The net (porous plate gel) had pores 1.8 mm in diameter, a pore ratio (area ratio) of 20% and a thickness of 1.2 mm.

The cooling solidification and partial dehydration under vacuum procedures were repeated with the same mixed aqueous solution of polyvinyl alcohol, glycerin and i-carrageenan as mentioned above to give 70 pieces of the same net (covering material).

Twelve adult dogs weighing 8–10 Kg were intravenously administered with 20 mg (bodyweight Kg$^{-1}$) of Isozol and completely depilated on the abdomen. The depilated region was applied with an electric iron (90°–110° C.) for 2 seconds to develop second-degree burn (44×43 cm). The burn was allowed untreated for 16 hours to induce infection (suppuration). There was observed continued production of much exudate (pus). The burned surfaces of two of the dogs were covered respectively with three pieces of the net covering material of the invention (48×17 cm) and bound up with a bandage via gauze. The covering material, gauze and bandage were renewed every 24 hours. It was confirmed in the renewal that the exudate from the wound part was smoothly passed through the net and absorbed in the gauze and bandage. There was also observed in the exchanges of the bandage no adhesion at all between the wound part and the gauze or between the covering material and the wound part.

As there was observed no moistness in the bandage and gauze after 7 days, the wound was judged to have progressed toward recovery (dry state). It was then allowed to stand for additional 7 days. There was observed regeneration of the epidermis around the wound surface on the 16th day after development of the burn. Thereafter, the ulcerous region became smaller day by day and recovered on the 20th day in the two dogs.

COMPARATIVE EXAMPLE 2

The i-carrageenan in Example 2 was not employed, and the amount of glycerin embedded was further increased to prepare an aqueous suspension of 5.3 g of polyvinyl alcohol (water content 7% by weight), 111 g of glycerin and 84 g of water. By the same procedures as in Example 2 was produced an aqueous solution of 2.5% by weight of polyvinyl alcohol and 55.5 g of glycerin. From 135 g of the aqueous solution was produced 95 g of a gel in the same way as in Example 2. The same procedures were repeated to prepare 70 pieces of the gel (covering material).

Three pieces of the net gel were applied respectively to the suppurated wound surfaces of two of the adult dogs with burn producing much exudate obtained in Example 2. The gel was bound up with a bandage via gauze. The three were renewed every 24 hours. It was confirmed that the exudate from the wound part was smoothly passed through the net. There was observed in the exchanges of the bandage no hemorrhage due to adhesion between the wound part and the gauze or the one between the wound part and the covering material. As there was observed no moistness in the bandage and gauze after 7 days, the wound was judged to have progressed toward recovery (dry state). It was then allowed to stand for additional 3 days without renewal of the covering material, gauze and bandage. Then, a renewal was attempted to find that deformation (unevenly shrinked to ca. 42×15 cm) and a stiffening tendency of the covering material were observed and a part of the covering material was adhered to the wound part.

As a matter of fact, whereas the gel of the invention in Example 2 was neither deformed nor deteriorated when allowed to stand dry for 7 days after exposure to much exudate, absence of i-carrageenan, a high-viscosity water-soluble macromolecular substance causes problems when allowed to stand following exposure to much exudate even if the amount of glycerin embedded is increased. The latter example indicates that the material is not tolerable to air drying for 3 days.

EXAMPLE 3

A mixed aqueous suspension of 10.8 g of a powdered polyvinyl alcohol (degree of hydrolysis 99.2 mol.%, viscosity average degree of polymerization 2,400, viscosity of the 4% aqueous solution (20° C.) 60 cP) (water content 7% by weight), 100 g of glycerin, 10 g of -carrageenan and 79 g of water was subjected to steam sterilization under pressure at 120° C. for 35 min. and then stirred in a sterile room to give an aqueous solution of 2.5% by weight of the polyvinyl alcohol, 50% by weight of glycerin and 5% by weight of λ-carrageenan. Onto a polyethylene plate with projections (height of the projection 2 mm, density of the projections 120,000/m², shape of the projection cylinder 2.3 mm in diameter, total area occupied by the projections 50% and size of the plate 24×12 cm) which had been gas sterilized was poured 26 g of the aqueous solution, which was evenly applied by means of an aluminum plate (27 c 14×0.1 cm) (thickness of the application 1.8 mm). Cooling and solidification at −60° C. for 0.8 hour and vacuum dehydration for 4 hours gave 14.5 g of a net gel (ratio of dehydration 45% by weight).

Then, the covering material was cut to a size of 9×9 cm. The piece was placed on gauze (10×10 cm, 12 pieces piled, thickness ca. 1 cm) on which 6 pieces of filter paper (A4, diameter 11 cm) were additionally piled. Over the pile was sprayed a model exudate (sodium chloride 0.9% by weight, albumin 2% by weight, globulin 2% by weight, glucose 0.1% by weight, lactic acid 0.2% by weight, pH 9.2, 37° C.) at a flow rate of 0.1–1.5 g.cm$_{-2}$d$_{-1}$. The resulting covering material was transferred to a thermostat at 37° C. and allowed to stand for a predetermined period of time. Deformation (shrinkage) and deterioration of the covering material were observed to give the results shown in Table 1. In fact, when the exudate was smaller, it was resistant to air drying for at least 20 days (Table 1, a). When the exudate was larger, it was resistant to air drying for at least 4 days (Table 1, A), the deformation (shrinkage) being slight and almost indistinct and the original softness being kept unchanged. COMPARATIVE EXAMPLE 3

The λ-carrageenan used in Example 3 was replaced by corresponding increase in the amount of glycerin, and the same procedures were conducted to give a net gel (9×9 cm). In the same way as above, the net was placed on gauze, piled with filter paper, sprayed with the model exudate and air-dried. Deformation (shrinkage) and deterioration (stiffening) were observed to give the results shown in Table 1. In fact, there was almost no problem with a smaller amount of the exudate, but air drying for 2 days with a larger amount of the exudate produced deformation and a stiffening tendency.

tion, which was evenly applied by means of a spatula (applied thickness 0.7 mm). Cooling (solidification and molding) at −58° C. for 0.7 hour and subsequent dehydration under vacuum for 4 hours gave 63 g of a gel (net) (ratio of dehydration 30% by weight). The net had a pore diameter of 1.8 mm, a pore ratio of 20% and a thickness of ca. 0.8 mm. The net was placed in a polyethylene bag (100 cm×20 cm) which had been sterilized with gaseous propylene oxide, and the bag was closely sealed and allowed to stand overnitht in a refrigerator (−10° C.). There was no stiffening (freezing), and original softness, elasticity and touch were kept unchanged. A portion of the net from the polyethylene bag was cut to a piece 1 cm×1 cm in size, which was allowed to stand on a dish in a thermostat at 37° C. Weight loss after one month was as small as 10% by weight (6 mg) or less, the original softness, elasticity and touch being kept unchanged.

Ten pieces (1×1 cm) of the covering material prepared in the same way as above were immersed in 20 ml of physiological saline solution. The solid and the liquid were separated after 30 hours, and the aqueous phase was microscopically examined. There were no bacteria observed, and no bacteria were detected also in the culture test.

On the other hand, when 20 ml. of physiological saline solution was allowed to stand for 30 hours, a lot of bacterial colonies were developed in the culture test, although there were observed no bacteria by microscopic examination. It was found that bacteria as many as ca. $10^3$/ml were present in the above physiological saline solution allowed to stand for 30 hours.

TABLE 1

Moistening and air-drying test of the covering materials

| Class | Run No. | Components of the covering material (gel) | Flow of the model exudate (g · cm$^{-2}$ d$^{-1}$) | Moistening time | Air drying time | Covering Material after air-dried size (cm) | Stiffening* |
|---|---|---|---|---|---|---|---|
| Example 3 | a | Polyvinyl alcohol, λ-carrageenan, Glycerin | 0.1 | 1 day | 20 days | 8.8 × 8.6 | — |
|  | A |  | 1.5 | 1 day | 4 days | 8.8 × 8.5 | — |
| Comparative Example 3 | b | Polyvinyl alcohol, Glycerin | 0.1 | 1 day | 20 days | 8 × 8.3 | + |
|  | B |  | 1.5 | 1 day | 2 days | 8 × 7 | ++ |

*— No stiffening observed.
+ Slight reduction in softness.
++ Stiffened.

EXAMPLE 4

A mixed aqueous suspension of 5.4 g of a powdered polyvinyl alcohol (degree of hydrolysis 99.5 mol.%, viscosity average degree of polymerization 2,600, viscosity of the 4% aqueous solution (20° C.) 66 cP) (water content 7%), 90 g of propylene glycol, 60 g of 25% by weight aqueous solution of polyacrylic acid and 44 g of water was subjected to steam sterilization under pressure at 120° C. for 35 min. and then stirred in a sterile room. In the resulting mixture was dissolved 10 mg of crystalline powdered potassium penicillin G (sterile dried) (16,500 units) as an antimicrobial agent. There was obtained an aqueous solution of 50 ppm of the antimicrobial agent, 2.5% by weight of the polyvinyl alcohol, 45% by weight of propylene glycol and 7.5% by weight of the polyacrylic acid. Onto a polyurethane rubber plate with projections (height of the projection 1 mm, density of the projections 74,000/m$^2$, shape of the projection cylinder 1.8 mm in diameter, total area occupied by the projections 20%, size of the plate 100 cm×17 cm) which had been sterilized with gaseous propylene oxide was poured 90 g of the aqueous solu- As set forth above, the covering material of the invention was found to be effective in embedding and slowly releasing antimicrobial agents.

1. A process of treating a burn comprising applying to the surface of the burn a water-insoluble gel produced by applying an aqueous solution containing a polyvinyl alcohol with a degree of hydrolysis not less than 95 mol.% and a viscosity-average degree of polymerization not less than 1,500, a water-soluble C$_{2-20}$ polyhydric alcohol having 2–8 hydroxyl groups in the molecule and a high-viscosity water-soluble substance having a viscosity in 2% aqueous solution not lower than 300 cP at 25° C. selected from the group consisting of propylene-glycol ester of alginic acid, tragacanth gum, puleulan, arabia gum, gatty fum, karaya gum, dextrin, starch, Dioscoreaceae mucous substance, mucous Malvaceae, furcellaran, curdlan, methylcellulose, guar gum, locust bean gum, xanthan gum, agar, carrageenan, fucoidin, alginic acid, sodium alginate, alginic acid triethanolamine, pectin, agarose, carboxymethylcellulose, tamarind gum, gelatin, polyacrylic acid, sodium polyacrylate, polymethacrylic acid, polyvinylsulfonic acid, polyvinylpyridine, polyethylenimine, vinylimidazole-itaconic acid copolymer, poly (2,4-pentadiene-1-ol) and poly (N-vinyl-2-pyrrolidone), concentrations of said polyvinyl alcohol, said water-soluble polyhydric alcohol and said water-soluble high viscosity substance being adjusted respectively to 1.5–8% by weight, 10–85% by weight and 0.2–15% by weight, onto a flat or curved plate having 30,000–200,000 projections per $m^2$, the total area occupied by the projections being 10–70% to a thickness from 0.5 to 5 mm, cooling the applied plate to a temperature not higher than $-6°$ C. to solidify the solution and then subjecting the resulting mass to vacuum dehydration to a ratio of dehydration from 5% by weight to 95% by weight.

2. The process according to claim 1 additionally containing antimicrobial agents.

3. The process according to claim 1 or claim 2 wherein said water-soluble polyhydric alcohol is an aliphatic polyhydric alcohol containing 2–20 carbon atoms.

4. The process according to claim 1 or claim 2 wherein said water-soluble polyhydric alcohol is 1,2-propylene glycol, glycerin or D-sorbitol.

5. The process according to claim 1 wherein said water-soluble high-viscosity substance is pullulan, xanthan gum, tragacanth gum, carboxymethylcellulose, polyacrylic acid, i-carrageenan, λ-carrageenan or propylene glycol ester of alginic acid.

* * * * *